Figure 1:
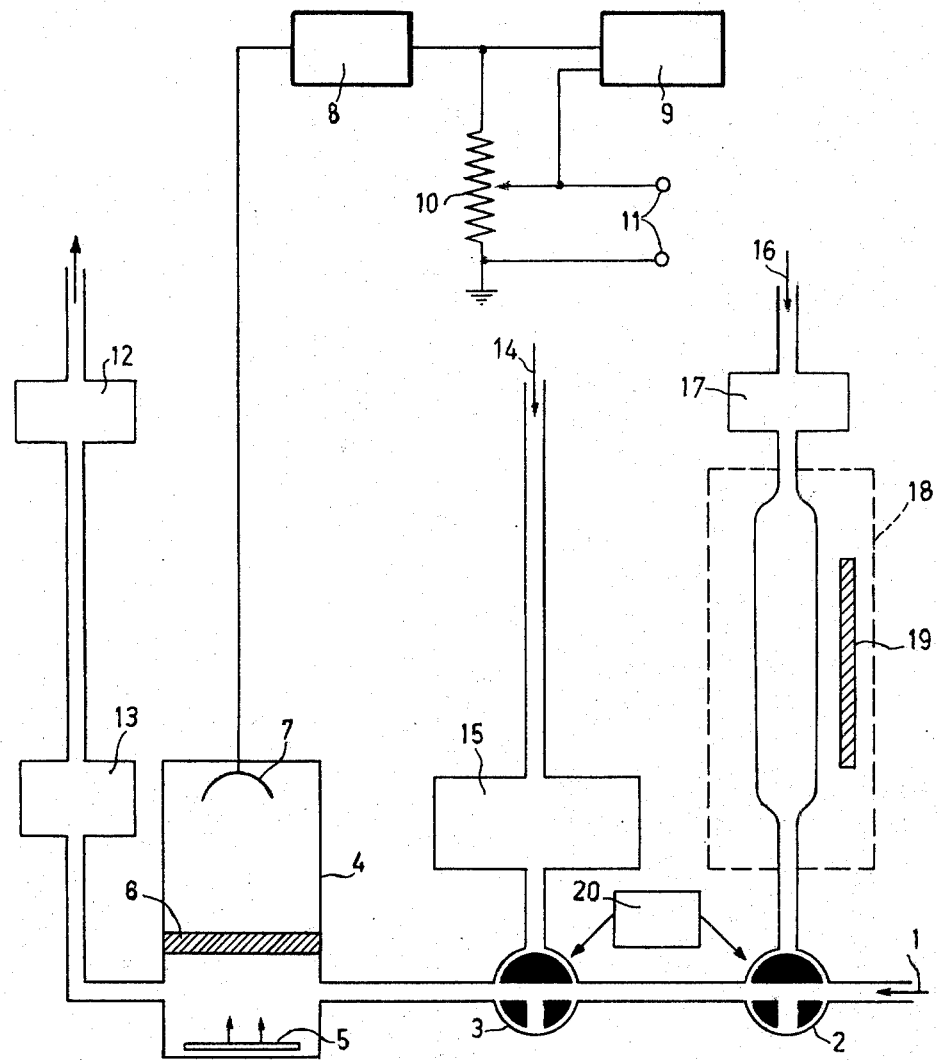

United States Patent [19]
van Heusden

[11] 3,975,159
[45] Aug. 17, 1976

[54] METHOD OF AND APPARATUS FOR DETERMINING THE OZONE CONTENTS OF GAS MIXTURES

[75] Inventor: Sybrandus van Heusden, Eindhoven, Netherlands

[73] Assignee: U.S. Philips Corporation, New York, N.Y.

[22] Filed: Mar. 13, 1975

[21] Appl. No.: 558,019

[30] Foreign Application Priority Data
Mar. 18, 1974 Netherlands............... 7403566

[52] U.S. Cl............................................ 23/232 E
[51] Int. Cl.².................................. G01N 21/26
[58] Field of Search.............................. 23/232

[56] References Cited
OTHER PUBLICATIONS
Bersis et al., Analyst 91, 499, (1966).
Bowman et al., Science 154, 1454, (1966).
Hodgeson et al., Anal. Chem. 42, 1795, (1970).

Primary Examiner—Robert M. Reese
Attorney, Agent, or Firm—Frank R. Trifari; Ronald L. Drumheller

[57] ABSTRACT

Determination of the ozone contents of gas mixtures by measuring the intensity of luminescent light emitted by a reaction of ozone with one of the halogenated fluorescein dyes eosin, erythrosin, cyanosin and Rose Bengal in combination with gallic acid.

1 Claim, 3 Drawing Figures

METHOD OF AND APPARATUS FOR DETERMINING THE OZONE CONTENTS OF GAS MIXTURES

The invention relates to a method of determining the ozone contents of gas mixtures and to an apparatus for carrying out the method.

A paper by J. A. Hodgeson et al. "Chemiluminescent measurement of atmospheric ozone" in Analytical Chemistry 42, 1795–1802 (1970) for example describes a method of determining the ozone contents in the atmosphere in which a chemiluminescent reaction of the ozone with a number of organic dyes, such as Rhodamine B, phenosafranine, fluorescein and erythrosin, is used. The dyes are absorbed at a pastille of activated silicagel. The intensity of the emitted light is a measure of the ozone concentration.

A disadvantage of this method is that in the reaction with the ozone the organic dye is consumed. As a result, the sensitivity of the reaction gradually decreases and the life of the pastille is comparatively short.

To eliminate this disadvantage D. Bersis and E. Vassiliou proposed in The Analyst 91, 499 (1966) to add to a solution of Rhodamine B a compound which serves as a mediator. This compound, gallic acid, reacts with ozone and transfers the energy liberated by the reaction to the Rhodamine B which in turn emits this energy in the form of radiation in a band which corresponds to that of the chemiluminescence of the direct reaction of ozone with Rhodamine B. However, in the presence of gallic acid no direct reaction of ozone and Rhodamine B takes place. Consequently the Rhodamine B is not consumed, which results in a reasonably constant sensitivity over a comparatively long period.

It was found, however, that in the case of intermittent measurements a certain starting effect occurs, both with Rhodamine B and with Rhodamine B together with gallic acid. In the former case initially too high a value is measured which decreases logarithmically to an approximately constant value and in the latter case initially too low a value is measured which logarithmically increases to an approximately constant value.

Other dyes which show chemiluminescence with ozone also were found to show these starting effects.

According to the invention, however, a small group of dyes was found which when combined with gallic acid exhibited no starting effect at all. Such combinations when used in a measuring apparatus are capable of unattendedly providing reliable measurements of the ozone concentration in air for 3 to 6 months.

The said dyes are the fluorescein dyes substituted with at least 4 bromine or iodine atoms, in particular eosin, erythrosin, cyanosin and Rose Bengal. The substances have the following structures:

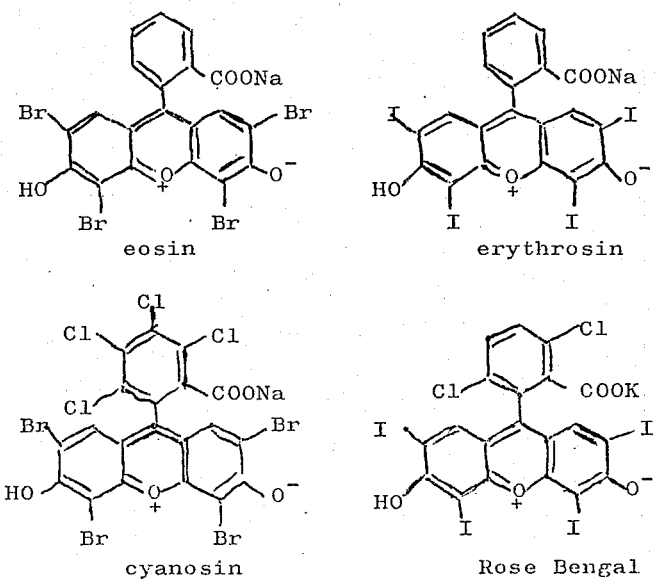

To prepare the reactant required for carrying out the invention a substrate coated with silicagel, a pastille of silicagel or another absorbent is impregnated with a solution of the dye, after which a few drops of a solution of gallic acid are added.

Figure 2:
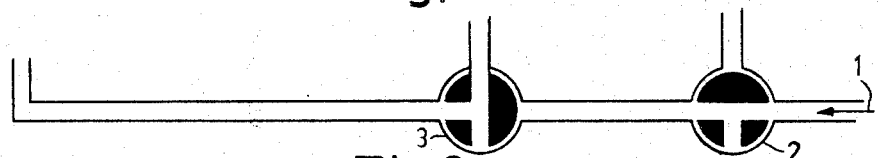
Figure 3:
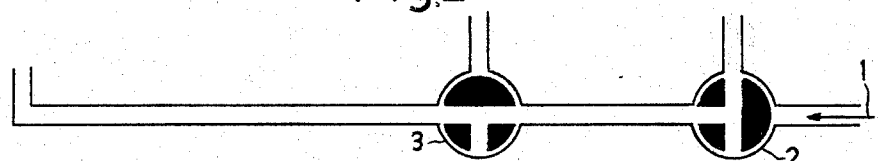

An apparatus for measuring the ozone content in gas mixtures will now be described more fully with reference to the accompanying diagrammatic drawings, in which FIG. 1 shows schematically the apparatus in the measuring condition and FIGS. 2 and 3 show a part of the apparatus in the conditions for zero determination and calibration respectively.

Referring now to FIG. 1, reference numeral 1 denotes an air inlet. The air flows through three-way valves 2 and 3 and in a space 4 comes into contact with an eosin/gallic acid preparation 5. The light emitted as a result of the chemiluminescent reaction impinges through a window 6 on a photomultiplier cell 7. The electric circuit of the cell comprises a current measuring device 8 and a control circuit 9 with a potentiometer 10. At an output 11 a voltage is measured and/or recorded. The air is drawn through the apparatus by means of a pump 12. A flow meter 13 indicates the rate of flow.

For zero determination the three-way valves 2 and 3 are in the positions shown in FIG. 2. In these positions the air enters through an inlet 14 to pass through a filter 15 in which the ozone is absorbed.

For calibration the three-way valves 2 and 3 are in the positions shown in FIG. 3. In these positions of the valves ambient air enters through an inlet 16 and is passed through a carbon filter 17 in which the ozone is absorbed. The air is then passed through a space 18 which is maintained at a constant temperature by a thermostat and accommodates an ozone generating mercury vapour lamp 14 which produces a constant amount of ozone per unit time. Readings at the terminals 11 are adjusted thereto.

By means of a timing switch 20 the three-way valves 2 and 3 are operated so as to produce a given sequence and a given duration of the cycle: zero determination-calibration-measurement.

What is claimed is:

1. In the method for determining the ozone content of a gas mixture by measuring the intensity of chemiluminescent light emitted from an organic compound exposed thereto, the improvement wherein the organic compound is mixed with gallic acid and is an organic dye selected from the group consisting of eosin, erythrosin, cyanosin and Rose Bengal.

* * * * *